United States Patent [19]
Plachetka et al.

[11] Patent Number: 6,077,539
[45] Date of Patent: Jun. 20, 2000

[54] TREATMENT OF MIGRAINE HEADACHE

[75] Inventors: John R. Plachetka, Chapel Hill, N.C.; Zakauddin T. Chowhan, Cockeyesville, Md.

[73] Assignee: Pozen, Inc., Chapel Hill, N.C.

[21] Appl. No.: 08/966,506

[22] Filed: Nov. 10, 1997

Related U.S. Application Data

[63] Continuation-in-part of application No. 08/748,332, Nov. 12, 1996, abandoned.

[51] Int. Cl.$^7$ .............................. A61K 9/22; A61K 9/24; A61K 9/26; A61K 9/28
[52] U.S. Cl. ...................... 424/474; 424/468; 424/469; 424/470; 424/472; 424/473
[58] Field of Search .................... 424/474, 482, 424/468, 469, 470, 472, 473, 475, 480

[56] References Cited

U.S. PATENT DOCUMENTS

| | | | |
|---|---|---|---|
| 4,024,279 | 5/1977 | Zor et al. | 424/319 |
| 4,380,540 | 4/1983 | Poyser et al. | 424/233 |
| 5,037,823 | 8/1991 | Jones et al. | 514/557 |
| 5,055,306 | 10/1991 | Barry et al. | 424/482 |
| 5,155,105 | 10/1992 | Jones et al. | 514/223.5 |
| 5,437,874 | 8/1995 | Bru et al. | 424/466 |
| 5,573,776 | 11/1996 | Harrison et al. | 424/435 |

FOREIGN PATENT DOCUMENTS

95/22947  8/1995  WIPO .

OTHER PUBLICATIONS

Albibi, "Metoclopramide: pharmacology and clinical application,"*Annals of Internal Medicine*,(1983)98: 86–95.

Anderson, "Double–blind study of naproxen vs placebo in the treatment of acute migraine attacks," *Cephalalgia* (1989) 9:29–32.

Bateman, "Extrapyramidal reactions to metoclopramide and prochlorperazine" *Quarterly Journal of Medicine* (1989) 71(264);307–311.

Baumel, "Migraine: A pharmacologic review with newer options and delivery modalities" *Neurology* (1994) 44 (Suppl 3) S13–S17.

Becker, "Pharmacokinetic aspects of a combination of metoclopramide and paracetamol. Results of a human kinetic study and consequences for migraine patients" *Arzneimittelforschung* (1992) 42(4):552–555 (inculding English language translation).

Boureau "Comparison of subcutaneous sumatriptan with usual acute treatments for migraine. French sumatriptan study group." *Eur Neurol* (1995) 35(5):264–269.

Capobianco "An overview of the diagnosis and pharmacologic treatment of migraine" *Mayo Clin Proc* (1996) 71:1055–1066.

Chabriat "Combined oral lysine acetylsalicylate and metoclopramide in the acute treatment of migraine: a multicentre double–blind placebo–controlled study" *Cephalalgia* (1994) 14: 297–300.

Chabriat "Combined Aspirin and Metoclopramide in the Acute Treatment of Migraine Attacks: A Review" *Headache Quarterly* (1997) 8:118–121.

(List continued on next page.)

*Primary Examiner*—James M. Spear
*Attorney, Agent, or Firm*—Michael A. Sanzo; Vinson & Elkins L.L.P.

[57] ABSTRACT

This invention comprises a non-vasoactive, supra-vasoactive syndrome ("SVS") minimized dosage form for treatment of migraine in a human comprising (i) rapid availability metoclopramide in at least about an effective local gastrointestinal amount; (ii) at least one long acting NSAID such as naproxen sodium in a therapeutically effective amount; (iii) wherein said dosage form is a coordinated dosage form; and, (iv) wherein the dosage form is absent 5HT agonist vasoactive agents, and preparation thereof. Acid-base stable dosage forms are noted. This invention further comprises methods of migraine treatment, and methods for rapid introduction of oral NSAID into the small bowel.

9 Claims, 5 Drawing Sheets

OTHER PUBLICATIONS

Chrubasik "Paracetamol and metoclopramide in fixed combination" *Med Montasschr Pharm* (1996) 19(4):110 (German language).

Cohen "Migraine Headache and the Managed Care Formulary" *Drugs Benefit Trends* (1996) 8(8) 28–30, 33–34,41.

Consumers Assoc. "Metoclopramide/analgesic combinations for migraine" *Drug and Therapeutics Bulletin* (1980) 18, No. 24: 95–96.

Dechant "Sumatriptan—A Review of its Pharmacodynamic and Pharmacokinetic Properties, and Therapeutic Efficacy in the Acute Treatement of Migraine and Cluster Headache" *Drugs* (1992) 43(5):776–798.

Diamond, "Do Non–Steroidal Anti–Inflammatory Agents Have a Role in the Treatment of Migraine Headaches" *Drugs* (1989) 37:755–760.

Edmeads "Four Steps In Managing Migraine" *Postgraduate Medicine* (1989) 85No. 6 121–124,127,128,131,132,134.

Eldor "Ergotamine–Metoclopramide for Migraine: Is it Enough?" *Cephalalgia* (1992) 446.

Ellis "The efficacy of metoclopramide in the treatment of migraine headache" *Annals of Emergency Medicine* (1993) Feb., 191–195.

Gamst "Oral Naproxen Formulations" *Scand J Gastro* (1989) 24 Suppl 163: 44–47.

Ganzini "The prevalence of metoclopramide–induced tardive dyskinesia and acute extrapyramidal movement disorders" *Arch Inter Med* (1993) 153: 1469–1475.

Greiff "Pharmacokinetic drug interactions with gastrointestinal motility modifying agents" *Clin Pharmacokinetics* (1994) 27(6): 447–461.

Gupta "Effect of Metoclopramide on Gastric Ulceration and Secretion in Albino Rats" *Arch. Int. Pharmacodyn* (1989) 297: 158–165.

Harrington "Metoclopramide—an updated review of its pharmacological properties and clinical use" *Drugs* (1983) 25: 451–494.

Hoernecke "Treatment of migraine attacks: combination of dihydroergotamine tartrate and paracetamol in comparison with individual drugs and placebo" *Med Klin* (1993) 88(11) 642–648.

Hughes, "Metoclopramide in migraine treatment" *Med J Aust.* (1997) 2 :580.

Hugues, "Repeated doses of combined oral lysine acetylsalicylate and metaclopramide in the acute treatment of migraine" *Headache* (1997) 37(7):452–454.

Johnson "Naproxen sodium in the treatment of migraine" *Cephalalgia* (1985) 5:10—May.

Kaa "Emergency department resource use by patients with migraine and asthma in a health maintenance organization" *Annals of Pharmacotherapy* (1995) 29:251–256.

Kandler, "Analgesic action of metoclopramide in prosthetic hip surgery" *Acta Anaesthesiol Scand* (1993) 37:49–53.

Klapper, "Toward a standard drug formulary for the treatment of headache" *Headache* (1995) Apr., 225–227.

Kumar, "Recent advances in the acute management of migraine and cluster headaches" *Journal of General Internal Medicine* (1994) 9:339–348.

Manniche, "The pharmacokinetics of the individual constituents of an aspirin–metoclopramide combination (Migravess)" *Curr Med Res Opin* (1984) 9: 153–156.

Mathew, "Serotonin 1D (5–HT1D) agonists and other agents in acute migraine" *Advances in Headache*, (1997) 15(1): 61–81.

Mohnot, "Treatment of Intractable Headaches" *Neurology* (1986) 36(Suppl 1):101.

Oral Sumatriptan Group, "A study to compare Oral sumatriptan with oral aspirin plus oral metoclopramide in the Acute treatment of migraine" *Eur Neurol* (1992) 32: 177–184.

Ottervanger, "Ketorolac for Severe Migraine" *Medical Science Bulletin* (1994) 26(6):49.

Peroutka, "Dopamine and Migraine" *Neurology* (1997) 49: 650–656.

Pfaffenrath, "Analgesics and NSAIDS in the treatment of the acute migraine attack" *Cephalalgia* (1995) Suppl 15: 14–20.

Pini, "Disposition of Naproxen After Oral Administration During and Between Migraine Attacks" *Headache* (1993) 33: 191–194.

Plosker, "Sumatriptan: a reappraisal of its pharmacology and therapeutic efficacy in the acute treatment of migraine and cluster headache" *Drugs* (1994) 47(4): 622–651.

Pradalier, "Treatment Review: Non–Steroid Anti–Inflammatory Drugs in the Treatment and Long–Term Prevention of Migraine Attacks" *Headache* (1988) 28: 550–557.

Pryse–Phillips, "Guidelines for the diagnosis and management of migraine in clinical practice" *Can Med Assoc J* (1997) 156(9):1273–1287.

Ross–Lee "Single–dose pharmacokinetics of metoclopramide" *Eur J Clin Pharmacol*, (1981) 20: 465–471.

Ross–Lee "Asprin Pharmacokinetics in Migraine. The Effect of Metoclopramide" *Eur J Clin Pharmacol* (1983) 24:777–785.

Saadah, "Abortive migraine therapy with oral naproxen sodium plus metoclopramide plus ergotamine tartrate with caffeine" *Headache* (1992) 32:95–97.

Scherl, "Comparison of dihydroergotamine with metoclopramide versus meperidine with promethazine in the treatment of acute migraine" *Headache* (1995) 35: 256–259.

Schwarzberg, "Application of metoclopramide specificity in migraine attacks therapy" *Headache* (1994) 34: 439–441.

Scott, Dihydroergotamine: A Review of Its Use in the Treatment of Migraine and Other Headaches *Clinical Neuropharmacology* (1992) 15(4): 289–296.

Sevelius, "Bioavailability of Naproxen Sodium and its Relationship to Clinical Analgesic Effects" *Br J Clin Pharmac* (1980) 10: 259–263.

Silberstein, "Migraine Symptoms: results of a self–reported migraineurs" *Headache* (1995) 35(7): 387–396.

Tfelt–Hansen, "A double–blind study of metoclopramide in the treatment of migraine attacks" *J Neurol, Neurosurg, Psychiatry* (1980) 43: 396–371.

Tfelt–Hansen, "The effectiveness of combined oral lysine acetylsalicylate and metoclopramide compared with oral sumatriptan for migraine" *Lancet* (1995) 346: 923–926.

Tfelt–Hansen, "Kombinationen af oral lysin–acetylsalicylat og metoclopramid sammenlignet med oral sumatriptan I behandlingen af migraeneanfald" *Videnskab og Praksis* (1996) 158(45): 6435–6439 (with English language abstract).

Tfelt–Hansen, "Effervescent metoclopramide and aspirin (Migravess) versus effervescent aspirin or placebo for migraine attacks: a double–blind study" *Cephalalgia* (1984) 4:107–111.

Thomson, "A Study to Compare Oral Sumatriptan with Oral Aspirin plus Metoclopramide in the Acute Treatment of Migraine" *Eur Neurol* (1992) 32: 177–184.

Todd, "Naproxen: a reappraisal of its pharmacology, and therapeutic use in rheumatic diseases and pain states" *Drugs* (1990) 40 (1):91–137.

Tokola, "Effects of migraine attack and metoclopramide on the absorption of telfenamic acid" *Br J Clin Pharmac* (1984)17: 67–75.

Tokola, "Tolfenamic acid, metoclopramide, caffiene and their combinations in the treatment of migraine attacks," *Cephalalgia* (1984) 4: 253–263.

Volans, "The Effect of Metoclopramide on the Absorption of Effervescent Aspirin in Migraine" *Br J Clin Pharmac* (1975) 2: 57–63.

Von Seggern, "Cost considerations in headache treatment part 2: Acute migraine treatment" *Headache* (1996) 36(8): 493–502.

Wilkinson, "Migraine and cluster headache—their management with sumatriptan: a critical review of the current clinical experience" *Cephalalgia* (1995) 15:337–357.

Wright, "Linearity of Metoclopramide Kinetics at doses of 5–20 mg." *Br J Clin Pharmac* (1988) 26: 469–473.

Kirby, "Effect of Metoclopramide, Bethanechol, and Lopramide on Gastric Residence Time, Gastric Emptying, and Mouth-to-Cecum Transit Time" *Pharmacotherapy* (1989) 9(4): 226–231.

TREATMENT OF MIGRAINE HEADACHE

RELATED APPLICATION

This application is a continuation-in-part of U.S. application Ser. No. 08/748,332 filed Nov. 12, 1996 now abandoned.

FILED OF THE INVENTION

This invention comprises a non-vasoactive, supra-vasoactive syndrome ("SVS") minimized dosage form for treatment of migraine in a human comprising (i) rapid availability metoclopramide in at least about an effective local gastrointestinal amount; (ii) at least one long acting NSAID such as naproxen sodium in a therapeutically effective amount; (iii) wherein said dosage form is a coordinated dosage form; and, (iv) wherein the dosage form is absent 5HT agonist vasoactive agents, and preparation thereof. Acid-base stable dosage forms are noted. This invention further comprises methods of migraine treatment, and methods for rapid introduction of oral NSAID into the small bowel.

BACKGROUND

Migraine is a painful syndrome characterized by unilateral, pulsating headaches, nausea, vomiting, and sensitivity to light and sounds. It is generally accepted that 23 million Americans suffer from migraine and that the incidence has been increasing over the last decade.

There are a number of recognized migraine therapeutic drugs. One recognized treatment for migraine is the administration of ergotamine or ergotamine-like agents. Another treatment is the administration of newer therapeutic agents known as serotonin agonists or 5HT agonists. Yet another treatment involves the administration of caffeine with ergots or other pharmacologic agents. While no more than sporadically effective, all of these conventional art recognized migraine drugs are thought to initially relieve migraine predominantly by causing vasoconstriction. Unfortunately, these conventional art recognized migraine drugs are associated with significant negative side effects that are linked to excessive vasoactivity in regions of the body not involved in the pathogenesis of migraine. This remote vasoactivity is an effect without any therapeutic benefit to the treatment of migraine. These vasoactive drugs are, in fact, contraindicated in patients with coexisting cardiovascular diseases, or the risk of cardiovascular diseases, such as hypertension, coronary artery disease, or peripheral vascular diseases. Other reported significant side effects are chest pain or pressure, flushing, generalized tingling sensations, nausea, vomiting, pain in the legs and arms, asthenia, drowsiness, and dizziness. In addition, agents such as ergots and caffeine are potentially addictive with well document withdrawal symptoms. Acute ergotism is a particularly pernicious side effect of ergot drugs, and is characterized by severe central and peripheral vasoconstriction, sometimes resulting in amputation of the affected limbs and/or digits, nausea, vomiting, diarrhea, colic, headache, vertigo, paresthesia, and possibly convulsive seizures. Chronic ergotism is characterized by intermittent claudication, muscle pains, numbness, and cold extremities as well as other gastrointestinal and CNS side effects.

The recognized migraine drugs act most quickly when they are administered by the parenteral route. Of course, no matter how administered, therapeutic relief of migraine is often not obtained. When given orally, the recognized migraine drugs act significantly more slowly than when parenterally administered such that pain relief, when obtained, may not be apparent for up to 2–3 hours post-administration. Considering the contraindications, risk of side effects, and slow onset of action of the ergot preparations and the new serotonin agonists when given orally, an improved migraine drug formulation for oral administration is needed for millions of migraine sufferers.

In some forms of migraine, certain patients have found total or partial relief with the use of non-prescription analgesics such as acetaminophen, aspirin, ibuprofen, and other non-steroidal anti-inflammatory agents, including naproxen and naproxen sodium. However, these agents, when taken alone, are rarely effective in providing complete and rapid relief of all the symptoms of migraine, especially when the symptoms of the attack already include nausea or vomiting. Moreover, there onset of action is slow such that relief sometimes does not occur for at least several hours.

As outlined by K. M. A. Welch (*New Engl J Med*, 1993:329; 1476–1483), the initial dosages of the analgesics useful for the treatment of migraine are: aspirin, 500–650 mg; acetaminophen, 500 mg; naproxen sodium, 750–825 mg; tolfenamic acid, 200–400 mg; and, ibuprofen 200 mg. After oral dosing, peak plasma concentrations in subjects not experiencing a migraine attack usually occur at or about 1 hour for aspirin and acetaminophen, and between 1–2 hours for naproxen sodium, tolfenamic acid, and ibuprofen.

It is of particular importance to note, however, that absorption of these and other agents during a migraine attack has been shown to be impaired in comparison with absorption rates when no migraine attack is occurring. Without being bound by any particular theory, it is believed that the observed slower absorption, and delayed plasma peak and onset of therapeutic action, is due to gastric stasis during migraine attacks.

Migraine attacks are debilitating to migraine sufferers. A migraine drug formulation that is
 (i) is side-effect reduced or side effect free both in being
  (i)(a) ergotism-free, and,
  (i)(b) absent supra-vasoactive response, and which exhibits a relief profile that represents
 (ii) a statistically significant increase in the percentage of subjects who respond within 1 hour of administration, and, in some groups,
 (iii) less than about 30% relapse within the 4 to 24 hour post-administration period (and preferably less than about 20%) represents a significant and surprising advance in migraine therapy.

Thus, non-vasoactive side-effect reduced or side effect free therapy requires exclusion of vasoactive agents like the ergots, serotonin agonists such as sumatriptan (including related 5HT agonist heterocyclic compounds as described in U.S. Pat. No. 4,816,470 to Dowle et al., the teachings of which are incorporated by reference) and caffeine. Of particular note is a migraine drug formulation that is delivered in a "sequential dissolve manner" reduces, prevents, or eliminates gastric stasis and the nausea/vomiting noted to occur with a migraine attack and allows for a faster rate of absorption of the presently recognized migraine drugs. This "side-effect reduced/absorption enhanced" formulation will, in turn, provide enhanced therapeutic effect compared to single administration of the analgesic alone. As more fully defined below, "enhanced" indicates that relief will be faster, or observed in a greater number of migraine headaches, or in a greater number of migraine sufferers, and with a significantly reduced incidence and/or severity of side-effects, or a broader group of symptoms will be relieved. Enhanced also includes the abortion of incipient migraine attacks.

One nausea relieving gastric absorption and gastric motility enhancing agent is metoclopramide. Metoclopramide has been described as having a minimal level of 5HT-3 antagonist properties. Such properties are not believed to rise to the level of a therapeutic analgesic. It is noted that parenteral administration of metoclopramide has been associated with relief of migraine symptoms. However, oral administration of metoclopramide has not been found to provide migraine relief. Thus, as a sole therapeutic agent for migraine relief, orally administered metoclopramide has not been known to be therapeutically effective. Metoclopramide does have potent anti-nausea and anti-vomiting properties. As nausea and vomiting are associated with is migraine attacks, metoclopramide given parenterally can provide symptomatic relief of these symptoms of migraine. Oral administration of metoclopramide formulations currently available are absorbed too slowly to provide adequate and timely relief of migraine associated nausea and vomiting. One formulation described in U.S. Pat. No. 4,380,540 to Poyser et al. discloses aspirin intermixed with metoclopramide, without reference to NSAID. U.S. Pat. No. 4,380,540 does not teach or suggest separating the acid aspirin component from the basic metoclopramide component. In fact, U.S. Pat. No. 4,380,540 particularly notes the uniform dispersion of metoclopramide throughout the aspirin. It is noted that metoclopramide is a proton acceptor (basic) as the active moiety, and even acid salts of metoclopramide are proton acceptors (Lewis base) in the dissolved state. When in chemical contact in tablets, metoclopramide and an acid analgesic such as aspirin or NSAID will experience unacceptable degradation (over 5%) in a matter of two to three weeks at ambient (about 150 to about 20° C.) and further about 25% degradation or deactivation in three weeks.

Given by the intravenous route, peak plasma levels of metoclopramide occur in 5 minutes. Given by the oral route, conventional tablets of metoclopramide provide peak plasma levels much more slowly with peak plasma levels occurring between one and two hours in subjects experiencing a migraine attack. The therapeutic literature suggests that the minimum oral dose for relief of nausea is 10 mg during a migraine episode. From onset, the antinausea action of metoclopramide appears to be at least 45–90 minutes using conventional tablets given orally. However, it has now been discovered that local improvement in gastric motility can be observed in some subjects with oral doses as low as about 1 mg, but more commonly from about 4 mg to about 20 mg, with particular emphasis from about 5 to less than about 10 mg, and further dependent on broad distribution over the surface of the gastric mucosa (usually in the solubilized form). As noted below, a dosage of metoclopramide that performs this function is termed an effective local gastric concentration. Without being bound by any particular theory, it is believed that in a migraineur having a migraine attack, metoclopramide locally available (i e., in the stomach and at the pyloric sphincter) facilitates relaxation of the pylorus otherwise in stasis, which immediately introduces the NSAID into the small bowl, the site of absorption for the NSAID. Such pyloric relaxation is a possible result of desensitization of the gastrointestinal tract to systemic neurotransmitters.

Headache recurrence after successful initial treatment is another weakness of some currently available anti-migraine preparations. That is, after a dosage of a therapeutic agent has been administered to a subject in an amount to initially effectively treat a migraine attack, and migraine palliation has been observed, migraine symptoms occur again from as soon as about 1–8 hours after first relief to about 12 to 24 hours later. It will be appreciated that individual migraineurs display individualized symptoms and timing for this phenomenon as will treatment with particular therapeutic agents.

The headache which occurs under the circumstances described above has been variously and interchangeably termed a "rebound," "relapse," "recurrent," "follow on," or "secondary" headache. The terms not withstanding, it is presently unknown as to whether this later headache is a continuation of the physiological chain of events that caused original headache, or a new headache due to other or repeated, but unrelated, underlying pathology. It is also possible that the follow on headache is a response to therapeutic agents which initially were successful in treating the initial migraine symptoms. The terms "rebound," "relapse," "recurrent" "follow on," and "secondary" (as defined below) are considered synonymous as used herein without inferring a mechanism or cause of migraine headache.

It has been reported that of the 50 to 70% of patients who experience migraine symptom relief within 2 hours from initial dosing with a 5HT agonist, 30–50% experience migraine symptoms again within the next 1–24 hours. In view of the extreme discomfort and long duration of pain that characterizes migraine headaches, a therapy that reduces or avoids rebound migraine is of substantial importance.

In the practice of this invention, of the analgesic agents mentioned above, the NSAID, naproxen sodium, is particularly useful agent to prevent the relapse headache. While it has not previously been found particularly useful, in the formulation and method of this invention, it has been discovered that its 13 hour half-life and long duration of action is useful when coupled with metoclopramide in specific formulations. Furthermore, naproxen sodium is non-vasoactive in the sense of direct vasoactivity. This is established by standard pharmacologic methods utilized to determine vasoactivity, with particular reference to The *Pharmacological Basis of Therapeutics,* Ed. L. S. Goodman and A. Gilman, eighth edition (Pergamon Press, New York 1990) the teachings of which are incorporated by reference.

A novel oral unit dosage form containing the active ingredients of metoclopramide and naproxen sodium, and absent caffeine, ergot drugs or other 5HT agonists is a formulation that will provide improved therapeutic non-vasoactive migraine relief with reduced side effects and reduced incidence of relapse. Naproxen tablets and metoclopramide tablets (and other dosage forms of these drugs) are commercially available. The available dosage forms are inadequate to provide for rapid sequential dissolution, rapid absorption and, ultimately, rapid, complete and long-lasting migraine symptom relief.

The intended therapeutic result, i.e., rapid, complete, and long-lasting migraine symptom relief, is produced with a unit dosage form that allows the metoclopramide component to dissolve first and extremely quickly, followed within a few minutes by the rapid dissolution and absorption of the naproxen sodium component. Particular excipients, compaction pressures and particles affect such mobilization, and particular note is made of naproxen sodium crystals in the 10 $\mu$m to 200 $\mu$m range (more particularly about 90 $\mu$m to about 150 $\mu$m) which particle sizes assist in permitting rapid absorption. Such a dosage form speeds the absorption of both active ingredients producing an enhanced therapeutic effect in the treatment of migraine.

Note is made of certain publications presenting aspects of the therapeutic treatment of migraine, the teachings of which are incorporated by reference: 1. "Treatment of the migraine attack." Silberstein S. D.; *Current Opinion in Neurology* 1994;7:258–263; 2. "Drug therapy of migraine." Welch, K. M. A.; *New Engl J Med;* 1993;329: 1476–1483; 3. "Recent advances in the acute management of migraine and cluster headaches." Kumar K. L.; *J Gen Int Med* 1994;9:339–348; 4. "Abortive Migraine Therapy with Oral Naproxen Sodium Plus Metoclopramide Plus Ergotamine Tartrate With Caffeine" Saadah, H., *Headache,* 32:95–97 (1992); and "Pharmacokinetic aspects of combination of metoclopramide and paracetamol. Results of human kinetic study and consequences for migraine patients." Becker, *Arzneimittelforshung,* 42(4), 552–555 (1992).

SUMMARY OF THE INVENTION

This invention comprises a non-vasoactive, supra-vasoactive syndrome ("SVS") minimized dosage form for treatment of migraine in a human comprising (i) rapid availability metoclopramide in at least about an effective local gastrointestinal amount, and, (ii) at least one long acting NSAID in a therapeutically effective amount, (iii) wherein said dosage form is a coordinated dosage form, and (iv) wherein the dosage form is absent 5HT agonist vasoactive agents. In particular embodiments, an acid base storage stable dosage form is noted. In some embodiments the dosage form contains metoclopramide in at least about 1 mg, or, at least about 5 mg, or at least about 10 mg. Expressed in a different fashion, the dosage form is such that metoclopramide is present in an amount that establishes a peak blood level of from about 1 to about 150 ng/ml. Particular note is made of a dosage form for rapid availability metoclopramide.

As to the NSAID of the dosage form it is selected from the group comprising flurbiprofen, ketoprofen, naproxen, oxaprozin, etodolac, indomethacin, ketorolac, nabumetane, mefenamic, piroxicam, or pharmaceutically acceptable salt thereof, with particular reference to naproxen and naproxen sodium. Fenamates are further noted in U.S. is Pat. No. 4,024,279 to Zor et al. In particular embodiments the naproxen or pharmaceutically acceptable salt thereof is present in an amount from about 100 mg to about 1500 mg, and particularly in an amount of from about 200 to about 600 mg. Expressed in a different fashion the naproxen or pharmaceutically acceptable salt thereof is present in an amount that establishes a peak blood level of from about 10 to about 150 mcg/ml of blood, and particularly from about 30 to about 80 mcg/ml. A noted dosage form is naproxen sodium comprising from about 200 to about 600 mg, and the metoclopramide comprising from about 3 to about 30 mg. In a one embodiment the dosage form further comprising at least one excipient selected from the group consisting of binding agents; fillers, disintegrants; and wetting agents. A particular dosage form presents naproxen sodium in crystalline form with the crystals are coated with excipient. Dosage forms including tablets are usefully in single or bilayer structure. One bilayer dosage form comprises a first layer and a second layer, and wherein the naproxen sodium is only in the first layer and metoclopramide is only in the second layer. In some embodiments, the second layer contains an interior and exterior portion with the metoclopramide in the exterior portion only. This dosage form in specific embodiments further comprises (i) a first layer containing an NSAID in granular form uniformly distributed throughout a matrix of pharmaceutically acceptable fillers, excipients, binding agents, is disintegrants, and lubricants, surrounded by (ii) a second layer having an interior and exterior portion, and having metoclopramide in crystalline form uniformly distributed throughout the exterior portion of said second layer wherein said interior portion comprises an interface between the exterior portion of said second layer the first layer, and wherein, (iii) the interior portion comprises from about 1% to about 15% of total tablet coating of said second layer. Particular note is made of an exterior portion of the second layer which comprises talc in an amount at least about 20% by weight of the exterior portion.

This invention further comprises a non-vasoactive, supra-vasoactive syndrome minimized method of therapeutic treatment of migraine in a human comprising co-timely administering metoclopramide in at least about an effective local gastrointestinal amount, and, further administering at least one long acting NSAID in a therapeutically effective amount, and wherein no 5HT agonist vasoactive agents are administered, optionally in unit dosage form. Particular note is made of this method wherein administering of metoclopramide is coordinated administering with said NSAID. In one embodiment of the method, administering metoclopramide comprising administering at least about 1 mg, 5 mg or 10 mg of metoclopramide. Otherwise expressed, the method comprises administering metoclopramide in at least about an effective local gastrointestinal concentration, or such as to establish a peak blood level of from about 1 to about 150 ng/ml. NSAIDs of note in this method are selected from the group comprising flurbiprofen, ketoprofen, naproxen, oxaprozin, etodolac, indomethacin, ketorolac, nabumetane, mefenamic, piroxicam, or pharmaceutically acceptable salt thereof, with specific not of naproxen and naproxen sodium. In one embodiment, the method comprises administering the naproxen or pharmaceutically acceptable salt such as naproxen sodium in an amount from about 100 mg to about 1500 mg, and particularly from about 200 to about 600 mg. Otherwise expressed, this embodiment includes administering naproxen or pharmaceutically acceptable salt thereof to the level establishing a peak blood level of from about 10 to about 150 mcg/ml of blood, and particularly establishing a peak blood plasma level is from about 30 to about 80 mcg/ml.

This method includes administering from about 200 to about 600 mg of naproxen sodium, and from about 5 to about 30 mg of metoclopramide, and further wherein the administering is orally, intranasally, rectally or sublingually, and wherein the administering metoclopramide rapid availability administering.

A particular method of administering the formulations of this invention includes unit dosage forms which comprise at least one excipient selected from the group consisting of binding agents; fillers, is disintegrants; or wetting agents, and optionally wherein the naproxen sodium is in crystalline form and further wherein said crystals are coated with excipient. Examples of dosage forms of this method included a bilayer dosage form of a first layer and a second layer, and wherein the naproxen sodium is only in the first layer and said metoclopramide is only in the second layer.

Physiologically stated, the method includes reaching a therapeutically effective amount of NSAID as measured in subject blood levels by at least about 60 minutes after administration and said level is maintained for at least about 8–12 hours after administration.

The invention yet further comprises a method of manufacturing acid-base storage stable uniform-coated unit dosage forms non-vasoactive, supra-vasoactive syndrome minimized dosage form forms non-treatment of migraine in a human comprising metoclopramide and an NSAID comprising the steps of (i) forming over an NSAID core (such as naproxen sodium) a coating layer having an interior and exterior portion by the steps of; (ii) applying as the interior portion of said layer a coating of a weight equal to from about 1% to about 8% of the core weight (and preferably 1–4% and more preferably 2–3%), wherein said coating is a pharmaceutically acceptable coating material and said coating material is absent metoclopramide; and thereafter (iii) drying said interior portion; and thereafter, (iv) applying over said dried interior portion an exterior portion comprising a coating of a weight equal to from about 6% to about 15% of the core weight, wherein said coating is a pharmaceutically acceptable tablet adhesion reduced coating material containing at least about 20% talc (dry weight of said exterior portion) and particularly about 23 to about 26% talc with particular reference to about 24% talc, and further comprises metoclopramide in crystalline form uniformly distributed throughout said exterior portion. In batch tablet manufacturing methods the preparation of coated tablets further comprises as to step (iv) of applying said exterior portion of a coating layer by the step of rotating in a tablet coating pan the NSAID cores with interior coating layer applied, said rotating being at a speed of from about 10 to about 25 rpm, wherein said rotation (with particular reference to agitating rotating) is accompanied by spraying said coating material from one to a plurality of spray guns mounted about 10 to 12 inches apart and 4 to 8 inches above the rotating pan tablets until the cores increase in weight from about 1% to about 15% or 20%, and particularly from about 4% to about 8%.

In yet another embodiment the invention includes method of rapidly introducing an NSAID administered via oral administration into the small bowel of a subject in gastric stasis by the step of administering oral metoclopramide in effective local gastrointestinal concentration in a co-timely coordinated non-spiking acid-base stable unit dosage form further including said NSAID. Particular reference is mad to naproxen including naproxen sodium and metoclopramide from about 5 to about 10 mg.

DETAILED DESCRIPTION OF THE INVENTION

Figure 1:
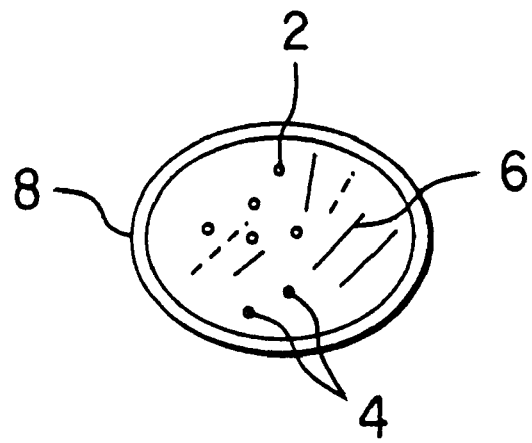
FIG. 1. is a diagrammatic side view of a single layer dosage form of the invention.

It has now been discovered that coordinated and co-timely administration of less of metoclopramide and a long acting non-steroidal anti-inflammatory drug (NSAID) therapeutically combined in a single layer tablet, bilayer tablet, or multilayer tablet for oral administration and possessing unique and specific formulation and dissolution characteristics provides an enhanced non-vasoactive therapeutic effect and relieves the symptoms of migraine, including, but not limited to headache pain and nausea, in patients in a superior manner to each individual component administered as a sole agent by use of a conventional tablet(s) of currently available products. Naproxen sodium is one such long acting NSAID. In particular embodiments, however, NSAID's other than long-acting NSAIDs are useful.

This invention will best be understood with reference to the following definitions:

A. "Long acting" in relation to NSAIDs shall mean a pharmacokinetics half-life of at least about 4–6 hours and preferably about 8–14 hours and a duration of action equal to or exceeding about 6–8 hours. Particular reference is made to flurbiprofen with a half-life of about 6 hours; ketoprofen with a half-life of about 2 to 4 hours; naproxen and naproxen sodium with half-lives of about 12 to 15 hours and about 12 to 13 hours respectively; oxaprozin with a half-life of about 42 to 50 hours; etodolac with a half-life of about 7 hours; indomethacin with a half-life of about 4 to 6 hours; ketorolac with a half-life of up to about 8–9 hours; nabumetane with a half-life of about 22 to 30 hours; mefenamic with a half-life of up to about 4 hours; and piroxicam with a half-life of about 4 to 6 hours. In the interest of clarity, naproxen is (S)-6-methoxy-a-methyl-2-naptha-leneacetic acid.

B. "Therapeutically effective amount" as to a drug dosage, shall mean that dosage that provides the specific pharmacological response for which the drug is administered in a significant number of subjects in need of such treatment. It is emphasized that migraine headache is not well understood and the etiology of particular migraines vary, as does the response to particular drugs. Thus reference to "specific pharmacological response for which the drug is administered in a significant number of subjects in need of such treatment" is a recognition that a "therapeutically effective amount," administered to a particular subject in a particular instance will not always abort migraine onset or relieve an actual migraine headache, even though such dosage is deemed a "therapeutically effective amount" by those skilled in the art. It is to be further understood that drug dosages are, in particular instances, measured as oral dosages, or parenteral or inhaled dosages or with reference to drug levels as measured in blood.

Particular reference is made to the following dosages of metoclopramide and NSAIDs, any of which are usefully combined into single dosage forms. Concerning dosages, as there is considerable variability as to the presenting condition of subjects, the skilled practitioner is expected to adjust dosages in such regard.

Metoclopramide monohydrochloride monohydrate is conveniently provided in conventional tablets of 5 and 10 mg and as a solution of 5 mg/5 ml and as an injection of 5 mg/ml. Although metoclopramide is not recognized by the FDA as an effective agent for the treatment of migraine, practitioners find doses of at least 10 mg by injection i.m. or intravenously to be particularly useful for the treatment of the nausea accompanying migraine. Oral doses of 10–20 mg are less useful because of it takes longer for therapeutic blood levels to be reached resulting in a slower onset of action.

Concerning NSAID dosages, as there is considerable variability as to the presenting condition of subjects, the skilled practitioner is expected to adjust dosages in such regard. Nevertheless it is noted that indomethacin is particularly useful when contained in tablets of from about 25 to 75 mg, in suppositories of about 50 mg, and in oral suspensions of about 25 mg/5 ml. A typical daily oral dosage of indomethacin is three 25 mg doses taken at intervals during one day amounting to 75 mg total, though daily doses of up to about 150 mg are also useful in some subjects. Sustained release dosage forms of indomethacin are also available and provide longer lasting blood levels than conventional tablets. In particular, a 25 mg sustained release dosage form can be used as an alternative to 25 mg three times daily or 75 mg twice daily can be substituted for 50 mg three times daily.

Ibuprofen is conveniently provided in tablets or caplets of 50, 100, 200, 300, 400, 600, and 800 mg and as a suspension of 100 mg/5 ml. Daily doses should not exceed 3200 mg and doses should be individualized. 200 mg–800 mg may be particularly useful when given 3–4 times daily.

Flurbiprofen is particularly useful when contained in tablets of from about 50 to 100 mg. Daily doses of about 100 to 500 mg, and particularly about 200 to 300 mg total are useful.

Ketoprofen is particularly useful when contained in capsules of from about 25 to 75 mg. Daily doses of about 100 to 500 mg, and particularly about 100 to 300 mg are useful, as is about 25 to about 50 mg every six to eight hours.

Naproxen is particularly useful when contained in tablets of from about 250 to about 500 mg, and in oral suspensions of about 125 mg/5 ml. For naproxen sodium, tablets of about 275 or about 550 mg are particularly useful. Initial doses of about 100 to 1250 mg, and particularly 350 to 800 mg are also useful with particular note of doses of about 550 mg. Plasma levels of about 70 µg/ml are noted.

Oxaprozin is notable for having a pharmacokinetics half-life of 42–50 hours and a bioavailability of 95%. It is usefully provided as caplets of 600 mg. Daily doses of 1200 mg have been found to be particularly useful and daily doses should not exceed 1800 mg or 26 mg/kg. The lowest effective dose should always be used.

Etodolac is usefully provided in capsules of 200 mg and 300 mg and tablets of 400 mg. Useful doses for acute pain are 200–400 mg every 6–8 hours not to exceed 1200 mg/day. Patients <60 kg are advised not to exceed doses of 20 mg/kg. Doses for other uses are also limited to 1200 mg per day in divided doses, particularly 2, 3, or 4 times daily.

Ketorolac is usefully provided in tablets of 10 mg and as a sterile parenteral preparation for injection in 15 mg/ml and 30 mg/ml dosage forms. Oral doses of up to 40 mg with particular reference to 10–30 mg per day and parenteral doses up to 120–150 mg per day have been useful in the amelioration of pain.

Nabumetane is usefully provided in tablets of 500 mg and 750 mg. Daily doses of up to 1500–2000 mg/day after an initial dose of 1000 mg is of particular use.

Mefenamic acid is particularly useful when contained in capsules of from about 250 mg. For acute pain such as migraine, an initial dosage of about 100 to 1000 mg and particularly about 500 mg is useful, though other dosages are required for specific subjects.

Meclofenamate sodium is usefully provided as capsules of 50 mg and 100 mg. Daily doses up to 400 mg are useful and in particular doses of 50–100 mg every 4–6 hours are useful for pain relief.

Piroxicam is particularly useful when contained in tablets of from about 10 to 20 mg. It is noted that, as steady state plasma concentrations are not reached until about 7 to 12 days of dosing, prophylactic use of piroxicam is a specific avenue of therapy to establish or a plasma concentration of greater than about 5 to 6 mg/ml. In such situation, coordination and co-timely administration of an 5HT agonist is achieved by the administration of the 5HT agonist approximately at the onset of a migraine.

C. "Abort-effective amount" as a subcategory of "therapeutically effective amount" is a dosage that, when compared to placebo, offers a statistically significant number of migraine attacks that do not progress to their usual course of causing the patient to feel moderate to severe headache pain accompanied by nausea, and/or sensitivity to light or sounds. In one embodiment, at least about 50% of incipient migraine attacks are aborted.

D. "Effective local gastrointestinal concentration" shall be understood to mean a dosage of metoclopramide that produces local is improvement in gastric motility, with particular reference to the pyloric sphincter, and most particularly to the pyloric sphincter in subjects undergoing a migraine attack. It is understood that, in some instances, an effective local gastrointestinal concentration of metoclopramide will overlap an abort-effective dosage when co-timely administered with an NSAID. While displaying variance from subject to subject, effective local gastrointestinal concentrations exhibit a peak blood level of from about 1 to about 150 ng/ml, and from about 50 to about 90 µg/ml in 20 minutes.

E. "Co-timely" as to metoclopramide/NSAID combination drug therapy shall mean administration of an NSAID while metoclopramide is present in at least about an effective local gastrointestinal concentration, and potentially in higher concentrations. In a preferred embodiment of co-timely drug administration, both drugs are administered in a single oral unit dosage form.

F. "Coordinated" in the practice of the present invention refers to administration of metoclopramide and at least one NSAID, wherein the metoclopramide is available in at least effective local gastrointestinal concentration in or at the gastrointestinal tract of a subject within at least about 1 to 30 minutes after administration and particularly about 5 minutes or less after administration, and more particularly about 3 minutes or less, and at least one NSAID will be initially available at a therapeutically effective level in a subject from at least about 30–60 minutes, and preferably from at least about 5 to 60 minutes, and continuing to about 12–24 hours after administration, but also wherein the therapeutically effective level of said NSAID is not attained until after metoclopramide is present in effective local gastrointestinal concentration.

Particularly note that coordinated unit dosage form is a dosage form that, upon administration provides the sequential delivery of the dosages as noted herein. Coordinated differs from co-timely in that coordinated is more specific as to the sequence in which specific drug levels are obtained.

Particularly note that coordinated unit dosage form is a dosage form that, upon administration provides the sequential delivery of the dosages as noted herein.

With marketed conventional oral NSAID formulations, the time to peak plasma levels for particular NSAIDs is as follows: flurbiprofen peaks in about 1 to 2 hours; ketoprofen peaks in about one-half to 2 hours; naproxen and naproxen sodium peak at about 2 to 4 hours and 1 to 2 hours respectively; oxaprozin peaks at about 3 to 5 hours; etodolac peaks at about 1 to 2 hours; indomethacin peaks at about 1 to 4 hours; ketorolac peaks at about one-half to 1 hour; nabumetane peaks at about 2.5 to 4 hours; mefenamic peaks at about 2 to 4 hours; meclofenamate peaks in 0.5–1 hours; and piroxicam peaks at about 3 to 5 hours.

G. "Rapid availability" as to metoclopramide in an oral dosage form shall be understood to be essentially the complete solubilization of metoclopramide from the oral dosage form within at least about 5 minutes from ingestion by a subject, and in some instances about 3 minutes. Clearly, an oral dosage form of metoclopramide which is liquid at the time of administration would also be a rapid availability form. In a combination dosage form of this invention which includes an NSAID, in particular embodiments, the NSAID will dissolve at a rate distinct from associated rapid availability metoclopramide. Beyond the characteristic of metoclopramide "rapid availability," dosage forms of the present invention provide blood levels which arise in the form of non-spiking metoclopramide peaks, and wherein the blood level of metoclopramide is maintained post-peak with high stability as defined below.

H. "Non-vasoactive" as it refers to the mechanism of action of drugs effective in migraine shall mean the substantial absence of demonstrated direct activity (either dilation or constriction) at therapeutic doses on either local or systemic arterial or venous blood vessels. Note is made that migraine attacks are associated with dilation of blood vessels in the head, and relief of a migraine headache is associated with the reduction of such vasodilation. In view of this, it will be appreciated that "non-vasoactive" as used to describe the compositions and method of the present invention contemplates a therapeutic mode of action that leads to a normalization of the abnormal blood vessel flow and geometry associated with a migraine-free state, but not by direct action on the vascular bed, but as an indirect action.

I. "5HT agonist vasoactive agents" shall refer to a class of 5HT agonists, including but not limited to 5HT 1-like agonists and all sub-types, with selective or non-selective vasoactivity on blood vessels including sumatriptan and all compounds either structurally and/or pharmacologically similar to it, ergotamine and all compounds either structurally and/or pharmacologically similar to it, and other serotonin agonists that exert a vasoactive effect. Metoclopramide, while of minimal 5HT agonist activity is excluded from the definition of 5HT vasoactive agents because of its insignificant activity on blood vessels at therapeutic doses.

Ergots shall mean that derivatives of 6-methylergoline. In naturally occurring forms this includes a substituent in the β configuration at position 8 and a double bond in ring D. Particular note is made of the amide derivatives of d-lysergic acid, a group of compounds which contain a double bond between C9 and C10 and thus belong to a family of 9-ergolene compounds. Many pharmaceutically active members of this class contain a methyl of hydroxymethyl group at position number 8, and are termed clavine alkaloids which include 9-ergolenes such as lysergol and 8-ergolenes such as elymoclavine. Additional note is made of ergocornine, ergocristine, α-ergocryptine and β-ergocryptine, and ergonovine. Synthetic derivatives include dihydroergotamine, dihydroergocristine, bromocriptine, the amides of lysergic acid (such as lysergic acid diethylamide, and lysergic acid hydroxybutamide). Also included are products of the methylation of the indole nitrogen of lysergic acid hydroxybutamide, which is methysergide.

Serotonin agonists shall mean that class of drugs which bind to and stimulate serotonin receptors (e.g., 5HT-1, 5HT-2 etc.).

As to methylxanthines, particular reference is made to caffeine, theophylline and theobromine (including soluble salts such as aminophylline and oxtriphylline).

Based on the foregoing, it is clear that in the context of the present invention metoclopramide is non-vasoactive at therapeutic doses. The non-vasoactivity of metoclopramide is established by a comparison with the 5HT agonist vasoactive agents and serotonin agonists, and methylxanthines.

J. "Migraine," unless otherwise specified, will be understood expansively to include be a subset of headache characterized by unusual severity, unilateral, throbbing, headache pain persisting for 4–72 hours and at least one or more of the following symptoms: nausea, vomiting, sensitivity to light and/or sounds with or without a preceding "aura" and visual "scotoma".

K. "Supra-vasoactive syndrome" or SVS shall mean that grouping of adverse reactions and clinical findings generally thought to be due to excessive vasoactivity remote from the intended site of action. SVS comprises one or more of the following symptoms and clinical findings: elevated blood pressure, reduced blood pressure, increased or reduced heart rate, cold extremities, tingling, flushing, feelings of neck or chest pressure, tightness, or heaviness, dizziness, hot or burning sensations, muscle pains, discomfort in the extremities, and frank angina or pain/discomfort of cardiac origin. Thus, "SVS-minimized" shall mean the substantial absence of SVS upon administration of an therapeutically effective amount of an anti-migraine preparation.

L. "Initial migraine relief" shall be understood to be the reduction or abolition of migraine symptoms from first onset of either a migraine attack or the precursor indicia of a migraine headache (i.e., aura and visual scotoma) in about a 24 hour period, and particularly in less than about a 6 hour period.

M. "Relapse headache" variously and interchangeably termed a "rebound," "relapse," "recurrent," "follow on," or secondary" headache shall mean headaches experienced most notably by that portion of the migraineur population that, while experiencing initial relief (or avoidance of migraine in the case of successfully abort-effective treated precursor symptoms) upon administration of any anti-migraine drug, experience repeated migraine or migraine symptoms within the next about 1 to 24 hours. Although it is presently unknown if this is a continuation of the original headache, a new headache either due to the ongoing underlying pathology or perhaps related to the administration of the therapeutic agents used initially to treat the migraine symptoms, these terms will be considered synonymous as used herein without inferring a mechanism or cause of the secondary headaches described above.

Figure 5A:
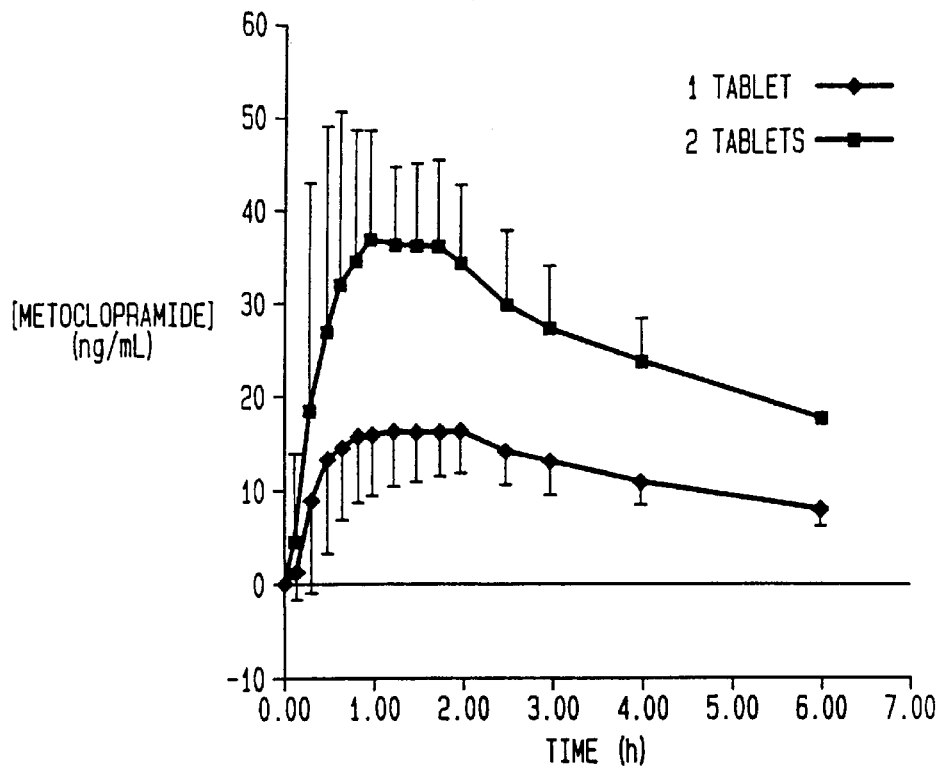
FIG. 5a is a plot of plasma concentrations of metoclopramide upon administration of tablet(s) of the present invention as disclosed in Tablet Example 4.
Figure 5B:
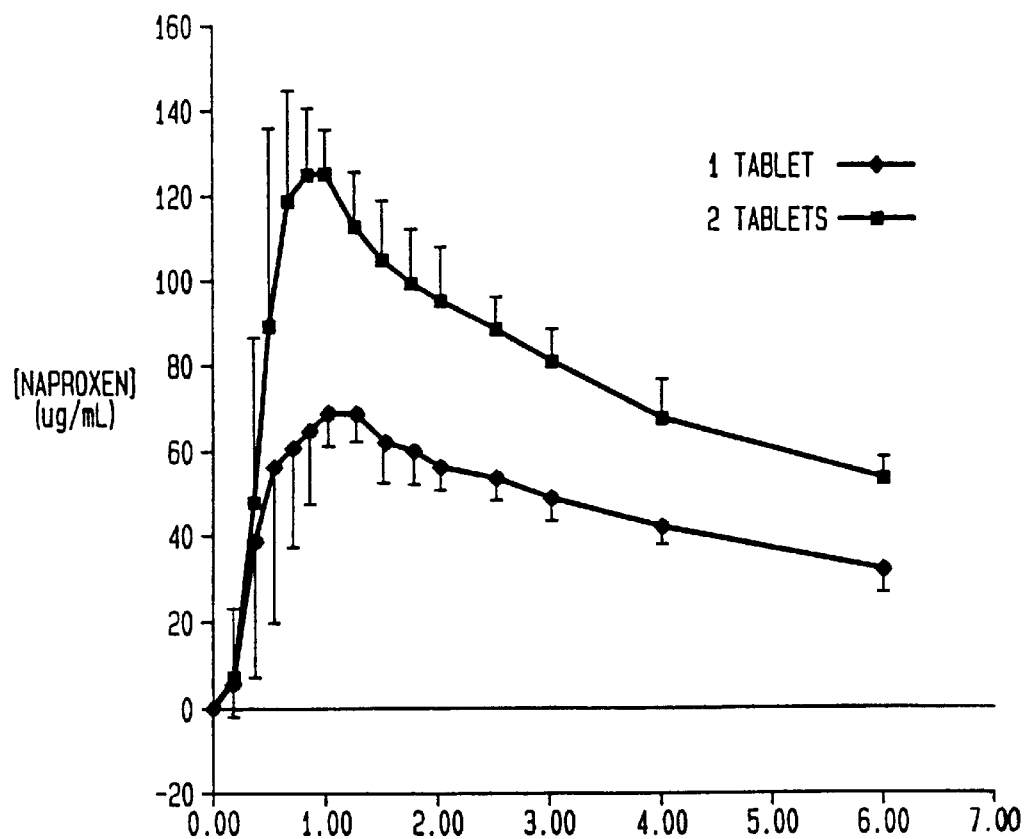
FIG. 5b is a plot of plasma concentrations of naproxen sodium upon administration of tablet(s) of the present invention as disclosed in Tablet Example 4.

N. "Unit dosage form" shall mean single drug administration entity. By way of example, a single tablet, capsule, dragee, or trochee (oral unit dosage forms), suppository, or syringe combining both metoclopramide and an NSAID would be a unit dosage form. Administration of a unit dosage form will result in blood levels of the NSAID required to produce a therapeutic effect within about the first hour after dosing and will still be present at least about 8–12 hours after initial dosing, and in particular instances, for as long as about 24 hours after dosing. Blood levels of the metoclopramide establishing effective local gastrointestinal concentration will be present within the first hour (with particular reference to the first 15 minutes post-administration, and more particularly the first 3 to 5 minutes) and should persist in measurable quantities for at least about 2–6 hours. Note the maintained blood levels apparent in the data of FIGS. 5a and 5b. In FIG. 5a, metoclopramide blood levels display non-spiking peaks with high stability.

Other combinations of these and other NSAIDS and metoclopramide likewise provide effective blood levels over the time periods specified above. It is preferred that the dosage form provide blood levels consistent with rapid initial migraine relief and a reduced incidence of relapse headache.

A particular type of unit dosage form is an "acid-base storage stable" unit dosage form. "Acid-base storage stable" unit form shall mean a dry unit dosage form of metoclopramide (a Lewis base, whether in the form of a free base or as an acid salt) in a tablet with an acid form of an NSAID wherein the potency of either active ingredient is not reduced by more than about 15% in 21 days storage at ambient temperature (15°–20° C.), nor by more than about 5% in 14 days. Acid base storage stable products of this invention in particular embodiments exhibit less than about 1% fall off in one year and more preferably less than about 1% fall off in three years. A further and surprising benefit of acid-base stability is the maintenance of early metoclopramide dissolution. Metoclopramide dissolution is retarded significantly only two weeks after formulation as a combined tablet without acid-base separation, as a combination of 500 mg naproxen sodium and 8 mg metoclopramide.

A "uniform-coated unit dosage form" shall mean a unit dosage form wherein the coating containing metoclopramide is between 85% and 115% with a standard deviation of no more than about 6.4.

O. "Enhanced therapeutic effect" in the context of this invention shall mean that the initial relief of migraine symptoms will occur more quickly and/or more extensively with the combination of two agents compared to the same doses of each component given alone in a conventional dosage; or that less than standard doses of one or both component(s) can be combined to provide relief of migraine symptoms at least comparable in speed and extent to that achieved with standard doses of either agent.

While the experienced clinician is able to monitor and adjust dosages as to each subject relative to the severity of the migraine attack and the presence of side-effects, generally available information on maximum common daily dosages of NSAIDs is useful as a cautionary guideline. In particular instances, however, exceeding these "maximum" doses is the therapeutic choice of the medical professional, it is noted that an indication of maximum daily doses in milligrams is as follows; flurbiprofen 300; ketoprofen 300; naproxen 1500, naproxen sodium 1375; oxaprozin 1800; etodolac 1200; indomethacin 150 to 200; ketorolac 120 mg i.m. and 40 oral; nabumetane 2000; mefenamic acid 1000; and piroxicam 20.

P. "Non-spiking" metoclopramide peaks shall mean a plasma is concentration of metoclopramide which remains within the limit of variation of its mean value for two or more consecutive time points. This is as disclosed in FIG. 5.

As seen in FIG. 5, administration of unit dosage forms of metoclopramide of the present invention produced non-spiking peak circulating levels of metoclopramide.

The data of FIG. 5 was obtained from 10 healthy volunteer subjects. On day 1, the subjects were administered one tablet of 500 mg naproxen sodium and 8 mg metoclopramide prepared as in Tablet Preparation Example 4 below. On day 4, two such tablets were administered. Venous blood samples were collected in Li⁺heparin tubes at the times shown. Red and white cells were then separated, and the supernatant deproteinated. The supernatant was then assayed for naproxen and metoclopramide and validated with reference standard by 40 times recrystallization.

Q. "High stability" in reference to sustained metoclopramide plasma levels shall mean less than a 10% deviation (post-$t_{max}$) from the mean over a 15 minute period within 6 hours of administration.

In generating the data of FIG. 5, an acid-base storage stable unit dosage form was employed. Without being bound by any particular theory, it is believed that the association of metoclopramide with $TiO_2$ of the tablet coating formulation moderates metoclopramide entry into the plasma in a formulation of the type disclosed in Tablet Preparation Example 4.

Without being bound by any particular theory, it is believed that by combining metoclopramide with an NSAID and particularly a long-acting NSAID one can achieve an enhanced therapeutic effect within the first 6 hours after dosing and a lower incidence of relapse headaches within the first 24–48 hours after initial dosing. Furthermore, this effect may be achievable with less than standard doses of one or both of these therapeutic agents which provides the additional benefit of a lower risk of side effects associated with either or both agents. For example, the combination of less than standard doses of metoclopramide and naproxen sodium may result in fewer gastrointestinal complications such as bleeding, ulceration, dyspepsia, heartburn, constipation, and dizziness, drowsiness, and headache due to naproxen sodium and less somnolence, agitation, restlessness, fatigue, and extrapyramidal symptoms including involuntary movements of the limbs, facial grimaces, torticollis, etc. due to the metoclopramide.

While not being bound by any particular theory, NSAIDs such as naproxen sodium are thought to relieve migraine pain through their known analgesic action, but may also relieve symptoms by reducing the neurogenic and vascular inflammation secondarily to their known anti-inflammatory actions or by other mechanisms such as, but not limited to, platelet inhibition or inhibition of prostaglandin synthesis. In addition, naproxen and naproxen sodium have half-lives on the order of 12–15 hours and produce a long-lasting effect.

In this context, the combination of metoclopramide and a long-acting NSAID in a single layer tablet or other solid dosage form, or in a bi- or multi layer tablet of the type described in this invention relieves nausea, improves gastrointestinal motility which enhances the speed of absorption of the NSAID, and provides an enhanced therapeutic effect against migraine symptoms in patients.

Without being bound to any particular shape or manufacturing process, in one embodiment, the delivery system for the combination of metoclopramide and naproxen sodium is a single layer tablet or solid dosage form or caplet containing appropriate excipients, agents to aid dissolution, lubricants, fillers, etc. and the active ingredients in the appropriate amounts. In a bilayer configuration, one portion of the tablet contains metoclopramide in the required dose and appropriate excipients, agents to aid dissolution, lubricants, fillers, etc., and is designed to dissolve up to 90% complete in the stomach in less than about 3 minutes, thus increasing gastrointestinal motility and controlling nausea. The effect of the rapid availability of metoclopramide is to accelerate delivery of the naproxen (or any other NSAID) to the small intestine which is the site of most rapid NSAID absorption. In a bilayer tablet embodiment, the second portion of the tablet will contain naproxen sodium in the required dose and appropriate excipients, agents to aid dissolution, lubricants, fillers, etc. and is designed to dissolve up to 90% complete after the metoclopramide portion of the tablet but after no longer than 10 minutes. In one embodiment of bilayer tablet preparation, once the two tablet components have been manufactured, they are combined into a single tablet. This process allows for different dosages of either tablet component (i.e. the metoclopramide component or the naproxen sodium component) to be usefully combined into a single tablet in an efficient way. In a particular embodiment, substantially each naproxen sodium crystal is coated with a rapid dissolving excipient material, conveniently, prior to tableting.

To establish the sequential dissolve aspect of dosage forms of the present invention, standard USP dissolution methods and apparatus are useful. In humans, the peak blood levels for both the metoclopramide and the naproxen sodium produced by the invention often occur at least 15–30 minutes more quickly than with standard USP tablets of metoclopramide and naproxen sodium, each in a separate tablet. Furthermore, migraine symptom relief will occur statistically more quickly and more often than with standard USP tablets of either metoclopramide or naproxen sodium.

Powder flow characteristics and powder compressibility are the main criteria for a successful production tablet. Rapid tablet disintegration is required to enhance dissolution. For compressibility, naproxen sodium is granulated. This involves increasing granule size through the addition of excipients that provide binding properties as well as disintegration properties. Granulation can be performed in a dry or wet state. Granulation methods include "slugging," a dry granulation method; low-shear granulation, high-shear granulation, a wet granulation method; and, fluidized-bed granulation, a wet granulation method.

Of these processes, slugging produced tablets of less hardness and greater friability than is suitable in particular applications. Low-shear, high-shear granulation, wet granulation and fluidized-bed granulation produced harder, less breakable tablets.

In particular formulations, it is useful to avoid disintegrants which alter flow characteristics adversely, or to use such disintegrants in amounts which adversely effect flow. For example, a mixture containing about 30–35% croscarmellose sodium, NF will exhibit less suitable flow characteristics resulting in reduced weight control and increased air entrapment ("capping") during tablet compression. Without being bound by any particular theory, it is believed that the fibrous texture of croscarmellose reduces the ability of blended materials to flow through is the hoppers and bins, thus increasing the variability in the delivery of the medicaments in the final dosage form. Similarly, crospovidone, NF and sodium starch glycolate, NF are less favored disintegrants.

TABLET EXAMPLE 1

A variety of combinations of metoclopramide and NSAIDs can be made into a single dosage form, either tablet, capsule, suppository, injections or other and consisting of a single layer or more than a single layer. In this example, a sequentially and rapidly dissolving single layer tablet of metoclopramide 8 mg combined with naproxen sodium 500 mg is conveniently available for use. Referring to FIG. 1, this single layer tablet contains naproxen sodium in crystalline form (2) and metoclopramide in crystalline form (4) each uniformly distributed throughout a matrix (6) of pharmaceutically acceptable fillers, excipients, binding agents, disintegrants, and lubricants (collectively, "carrier material"). A pharmaceutically acceptable tablet coating (8) surrounds the active ingredients and carrier materials. In one embodiment, the total weight of the carrier material is about 500–1,000 mg. In particular embodiments, carrier material comprises 50 mg to 2000 mg or more. In one embodiment, prior to compaction in a tablet, each crystal of naproxen sodium is coated with excipient. Particular note is made of the use of microcrystalline cellulose and magnesium stearate. In particular embodiments, coating naproxen sodium with hydroxypropyl methylcellulose 2910 and polyethylene 8000 is noted. A core bulking agent of lactose or lactose and a polymer film coating such as Opaspray® K-1-4210A or Opadry® YS-1-4215 (trademarks of Colorcon, West Point, Pa.) in a coating suspension is noted. In addition, povidone and talc are useful bulking agents for the tablet core.

Tablet stability is compromised in instances in which there is an "acid-base incompatibility" between the metoclopramide and the NSAID. For example, naproxen sodium (the more easily absorbed form of analgesic) is a crystalline solid that is freely soluble in water of neutral pH. Metoclopramide hydrochloride is a white crystalline substance that is freely soluble in water. The metoclopramide monohydrochloride base is more readily absorbed in the gastrointestinal tract. The basic salt of metoclopramide intimately mixed with acidic naproxen sodium cross-reacts in a matter of days causing reduction in tablet potency of at least about 5% in two weeks and about 20 to 25% or more in three weeks at ambient temperature. Thus, separation between the component active ingredients can be obtained by presenting either or both active ingredients in barrier coated form. In view of the importance of rapid availability of metoclopramide in a therapeutically effective dosage, an embodiment in which only the NSAID is barrier coated is noted. Suitable barrier type coating materials for naproxen sodium include OpaDry as is applied in combination with water for irrigation and talc. Other materials are shellac, hydroxypropyl methylcellulose phthalate, polyvinyl acetate phthalate, and cellulose acetate phthalate. Thin coatings, on the order of about 25–250 microns retards the availability of naproxen by no more than about 5 minutes, while substantially extending storage life of the combined formulation.

TABLET EXAMPLE 2

Figure 2:
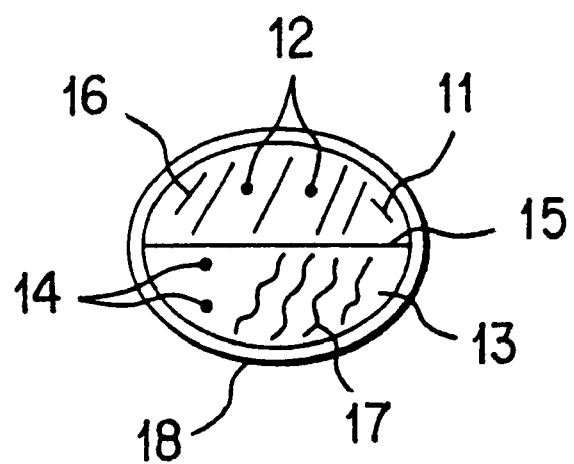
FIG. 2. is a diagrammatic side view of a bilayer dosage form of the invention.

FIG. 2. is an example, a sequentially and rapidly dissolving bilayer tablet of metoclopramide 16 mg combined with naproxen sodium 500 mg. Referring to FIG. 2, this bilayer tablet consists of a first layer (11) and a second layer (13). The first layer (11) contains naproxen sodium in crystalline form (12) uniformly distributed throughout a matrix (16) of pharmaceutically acceptable fillers, excipients, binding agents, disintegrants, and lubricants (collectively, "first carrier material"). The second layer (13) contains metoclopramide in crystalline form (14) uniformly distributed throughout a matrix (17) of pharmaceutically acceptable fillers, excipients, binding agents, disintegrants, and lubricants (collectively, "second carrier material"). A pharmaceutically acceptable tablet coating (18) surrounds the active ingredients and carrier materials. Dotted line 15 represents the interface between the two layers which are separately molded, poured, compressed or otherwise formed and joined by compression or other tablet forming means. In particular embodiments, the first carrier material and the second carrier material will be the same or different.

In one embodiment of a two layer tablet in which metoclopramide is in a matrix separated from the NSAID, the metoclopramide portion may be in effervescent formulation, which, upon addition to water, becomes a liquid, and the NSAID such as naproxen remains in solid form. Particular note is made of both an NSAID tablet remaining as a single lozenge, as well as in the form of numerous coated beads or granules (with particular reference to sizes within the 4 to 12 sieve range) acting as a slurry in the effervescent solution. A number of tableting techniques are described in *Pharmaceutical Dosage Forms and Drug Delivery Systems*, Ansel et al., Sixth Ed. (Williams & Wilkins, Media Penn., 1995) the teachings of which are incorporated herein by reference.

TABLET EXAMPLE 3

A particular embodiment of a tablet in which metoclopramide is in an effervescent matrix separated from the NSAID is as follows:

A. Metoclopramide: Metoclopramide in the form of an acid salt is prepared in a particle size of from about 4 to 10 mesh size (4.76 mm to 2.00 mm) formed by moistening blended powders and passing through a is screen or granulator. In this manner, 60 mg of metoclopramide are combined and 250 gm of a mixture of
   200 gm dried dibasic sodium phosphate
   477 gm sodium bicarbonate in dry powder
   252 gm tartaric acid in dry powder
   162 gm citric acid monohydrate.
B. Naproxen: 500 mg of naproxen sodium are compacted as granules with povidone k-29/32, 23.6 mg; microcrystalline cellulose, NF, 105.9 mg; croscarmellose sodium, NF, 13.5; talc, 27 mg; magnesium stearate, 5 mg.
C. The metoclopramide granules as prepared above and the naproxen are then combined into the two layer tablet as described in Tablet Example 2.

Figure 3:
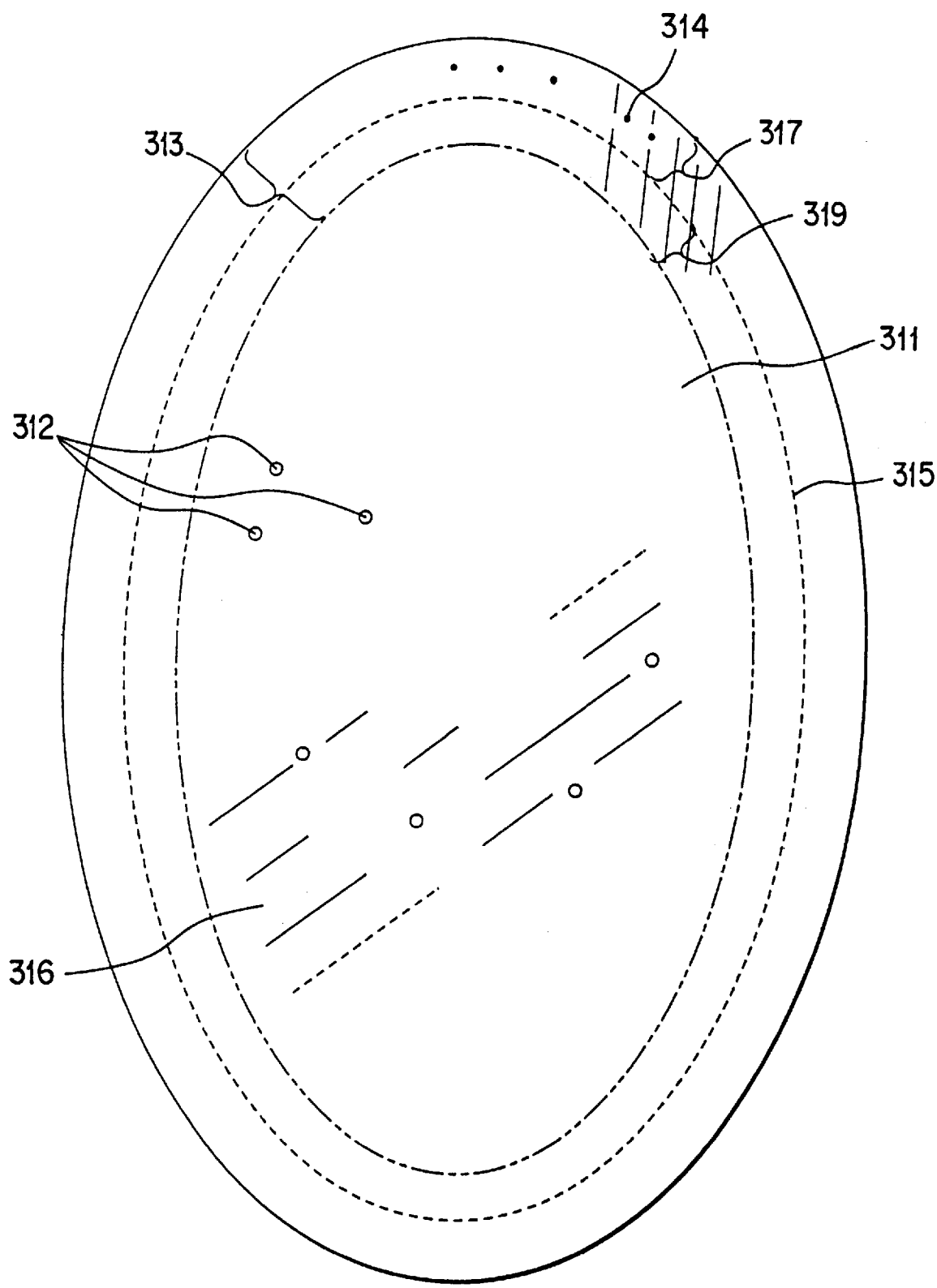
FIG. 3. is a diagrammatic side view of another bilayer dosage form of the invention.

FIG. 3. is another example, a sequentially and rapidly dissolving bilayer tablet of metoclopramide hydrochloride 8 mg combined with naproxen sodium 500 mg. Referring to FIG. 3, this bilayer tablet consists of a first layer (311) and a second layer (313) having an exterior portion (317) and an interior portion (319). The first layer (311) contains naproxen sodium granules in crystalline form (312) uniformly distributed throughout a matrix (316) of pharmaceutically acceptable fillers, excipients, binding agents, disintegrants, and lubricants (collectively, "first carrier material"), collectively a core. The second layer (313) contains metoclopramide hydrochloride in crystalline form (314) uniformly distributed throughout a the exterior portion of layer (313), is wherein (317) comprises a matrix of pharmaceutically acceptable tablet coating. This tablet coating (317) which also surrounds the layer of naproxen and carrier materials (311). Dotted line (315) represents the interface between the exterior portion of (313) and the interior portion (319), which interface in some embodiments is titanium dioxide, carnauba wax, shellac, cellulose acetate phthalate or the like. In this embodiment, interior portion (319) comprises about 2 to 3% of the coating material comprising (313) and particularly separates the naproxen layer or core from the metoclopramide. As depicted diagrammatically in FIG. 3., the portion of the coating layer below line (315) is comprised of the same pharmaceutically coating material as matrix (317). This architecture separates the acidic naproxen the basic form of metoclopramide.

In one embodiment, the naproxen containing portion is separately molded, poured, compressed or otherwise formed and joined by compression or other tablet forming means, and then spray coated with a coating material absent metoclopramide. Particular reference is made to an core coating over the NSAID core comprising HPMC, triethyl citrate, and TiO$_2$ applied in an aqueous spray. A coating of 1 to 10% and more particularly, 2 to 3% of the total coating weight are useful core coatings. Then later spray coatings of coating material which include metoclopramide hydrochloride are applied. The later coating further segregates metoclopramide in basic form from the acid form of NSAID such as naproxen. In one embodiment, a core coating comprising HPMC, triethyl citrate, TiO$_2$, and talc applied in an aqueous spray is used. Particular note is made of a later coating comprising (by weight of total weight of later or outer coating in a dry condition, i.e., absent water):

HPMC from about 35 to about 55% and particularly about 42 to about 47% and particularly about 45%;

Titanium dioxide from about 3 to about 8% and particularly about 4 to about 6% and particularly about 5%;

Triethylcitrate from about 0.05 to about 0.3% and particularly about 0.07 to about 0.2% and particularly about 0.1%;

Talc from at least about 17% and particularly from about 20 to about 35% and particularly about 21 to about 27% and particularly about 24%; and Metoclopramide from about 10 to about 40% and particularly about 20 to about 30% and particularly about 26%.

In one embodiment of preparation of a tablet of FIG. 3., metoclopramide hydrochloride is suspended in a coating solution that is applied to a core consisting of about 100–1000 mg of naproxen sodium, and about particularly 500 mg.

Preparation of a tablet of FIG. 3 requires particular attention to the application of metoclopramide to maintain acceptable tablet dosage uniformity ("uniform-coated unit dosage form"). Acceptable, here, is a coating uniform to between 85% and 115% of the intended dosage with a standard deviation of 6.4 or less. With pancoating methodology, it is important to note pan speed, movement of tablets across the tablet bed, spray temperature and spray coverage relative to the entire pan. Tablets sticking to each other or to the pan during coating will reduce uniformity. Thus, it is advantageous to apply a coating material that does not readily stick to the pan, and to agitate tablets ("agitating rotating") during coating such that tablets do not stick to each other. Employing a coating pan with baffles offers agitating rotation of the tablets being coated. A coating that does not cause tablets to stick to each other during agitating rotating in a coating pan is termed an "adhesion reduced" coating. Talc is a useful additive to provide an adhesion reduced coating. Talc in at least about 18%, and more particularly about 20% and most particularly at least about 24% of the dry weight of the metoclopramide containing outer portion is noted as adhesion reduced.

Figure 6:
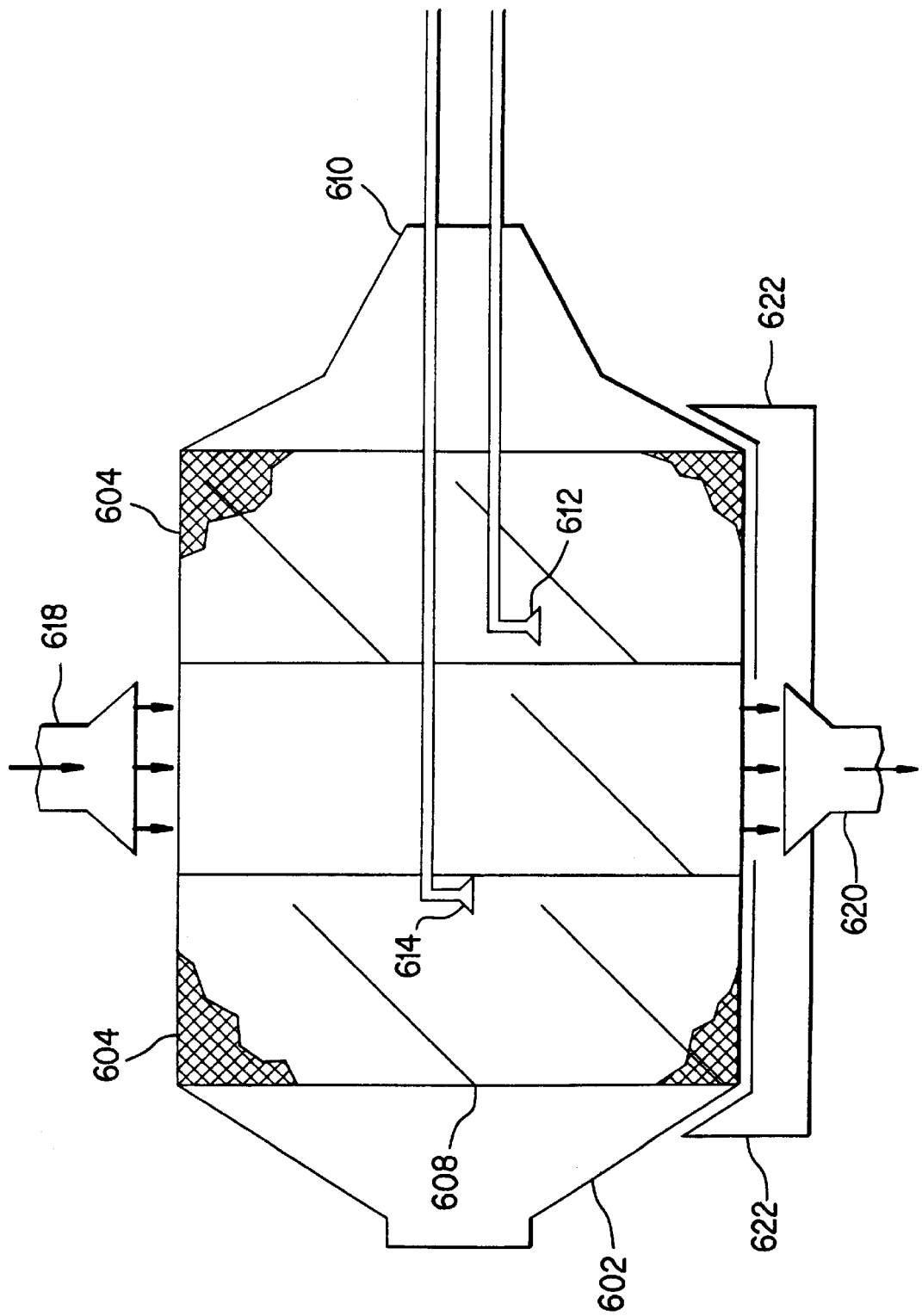
FIG. 6 is a diagrammatic cross section side view of a tablet coating pan with baffles and spray nozzles.

FIG. 6 provides a diagrammatic apparatus for tablet coating. A rotating coating pan (602) in normal operation is partially filled with tablet cores to be coated. In the depicted embodiment, screen panels (604) facilitate air circulation, and baffles (608) placed on the coating pan walls agitate tablet cores during rotation. Spray nozzles (612) and (614) is leading from a spray mixture reservoir and pump means (neither shown) through inlet (610) spray coating over tablet cores. An air source (618) introduces drying air into the coating pan from a heating and pumping source (not shown). Air exits through a vacuum outlet (620) as well as through screen panels (604). The coating pan is rotated by a rotating means (622).

Particular note is made of the efficacy of coating NSAID cores, particularly naproxen cores, with an atomized coating mixture while the cores are in a rotating pan. While there are a number of devices available, reference is made to the Driacoater/Vario 500/600 (Driam U.S.A., Spartanburg, Pa.) and spray guns such as the 460 Bink spray gun (Binks Manufacturing Company, Franklin Park Ill.)). Using two spray guns about 10 to 12 inches apart and 4 to 8 inches above the tablet bed is useful. A rotation speed of about 14 to 16 rpm for the pan is useful. Particular mention is made of the need for tablet movement in the pan to avoid tablet sticking and enhance coating uniformity.

TABLET PREPARATION EXAMPLE 4

Metoclopramide Film Coated Tablet

This acid-base storage stable uniform-coated unit dosage form presents metoclopramide as a film in the outermost portion of the tablet and separated from the naproxen sodium.

Final tablet formulation by weight
metoclopramide hydrochloride 8 mg
(i) metoclopramide containing coating (in percentage of total metoclopramide containing coating dry weight)

| | |
|---|---|
| hydroxypropyl methylcellulose | 45% ± 5% |
| titanium dioxide | 5% ± 2% |
| triethyl citrate | 0.1% ± 0.5% |
| metoclopramide | 26% ± 1% |
| talc | 24% ± 1% |

(ii) metoclopramide free coating (in percentage of total tablet dry weight)

| | |
|---|---|
| hydroxypropyl methylcellulose | 9% |
| titanium dioxide | 1% |
| triethyl citrate | 2% |
| naproxen core | |
| naproxen sodium | 500 mg |
| povidone k-29/32 | 23.6 mg |
| microcrystalline cellulose, NF, | 105.9 mg |
| croscarmellose sodium, NF | 13.5 |
| talc | 27 mg |
| magnesium stearate | 5 mg |

To prepare a two layer tablet as in FIG. 3., particular attention is paid to the application of the film coating. The naproxen cores were placed in the coating pan with baffles in place and with a rotation speed of about 14–16 rpm. From two spray guns mounted about 4 to 8 inches apart and 10 to 12 inches above the tablet bed, atomized metoclopramide free coating mixture was sprayed over the rotating pan until the cores increased from about 2% to about 3% in weight forming an interface. Continuous drying was performed by air input at about 65° C.±5°, and with an exhaust temperature of 45° C.±5°. With spraying at pressures when the atomizer is set at 2.0–4.0 bar yields a spray particle size of from about 10 µm to about 200 µm and averaging about 50 µm.

After the initial coating step, tablets were again spray coated in the rotating baffled pan, but now with a metoclopramide containing coating material until the tablet weight increased from about 8 to about 10% over the weight of the naproxen core. In this embodiment, spraying was conducted to apply 8 mg of metoclopramide to each tablet.

Tablets were then examined for uniformity of metoclopramide content in keeping with the requirement of a "uniform-coated unit dosage form." Testing the content of metoclopramide HCl confirmed that the metoclopramied in the coating of each tablet was between 85% and 115% of calculated dosage with a standard deviation of no more than 6.4.

Tablet Dissolution

A comparison of a dissolution times was made between unit dosage forms. Dissolution was determined by USP apparatus #2. By such apparatus, 70–80% represents essentially total dissolution (unless stirrer speeds are markedly increased). Data is presented for
(i) naproxen sodium and metoclopramide HCl, each in a separate layer but with the metoclopramide in a coating film (the tablet of Tablet Example 4)
(ii) naproxen sodium and metoclopramide HCl in a single matrix not acid-base stable, but newly made; and
(iii) naproxen sodium and metoclopramide HCl in a single matrix not acid-base stable, after 14 days storage at ambient temperature (15°–20° C.).

Figure 4:
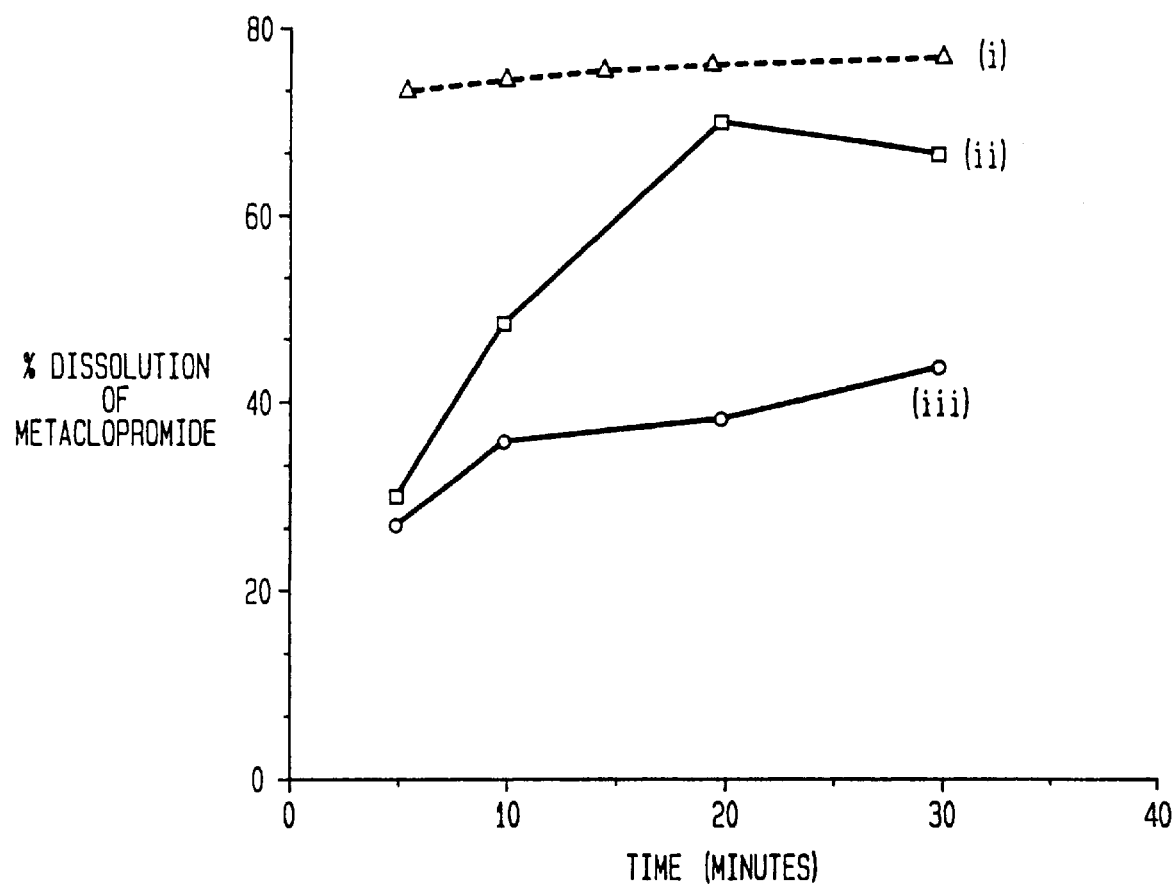
FIG. 4. is a comparative dissolution plot of the metoclopramide presented in a tablet coating layer and presented in a compressed tablet layer.

Rapid availability as to metoclopramide in an oral dosage of essentially the complete solubilization of metoclopramide from the oral dosage form within at least about 5 minutes from ingestion by a subject was observed in the in vitro modeling (using 0.01 M to 0.1 M HCl) for the tablet of Tablet Preparation Example 4. As seen in FIG. 4 the metaclopramide film coated tablet was observed to have total metaclopramide at least by the first time point of 5 minutes.

TREATMENT EXAMPLE 1

An adult female migraineur complains of a migraine attack consisting of typical migraine headache, nausea and sensitivity to light and sound. She is dosed with a single oral (single layer) tablet containing metoclopramide 8 mg and naproxen sodium 250 mg. Her symptoms start to diminish within one hour and by three hours she is completely is symptom free. No relapse over the next 48 hours is reported. Her pain relief occurs more quickly, and with longer uninterrupted relief than in the past.

TREATMENT EXAMPLE 2

An adult female migraineur is complaining of a migraine attack consisting of typical migraine headache, nausea and sensitivity to light and sound. She is dosed with a single oral (bilayer) tablet containing metoclopramide 16 mg and naproxen sodium 500 mg. Her symptoms start to diminish within one hour and by three hours she is completely symptom free and has no relapse over the next 48 hours. She experiences fewer adverse events than when she ingested 875 mg of naproxen sodium alone, especially gastrointestinal complaints.

TREATMENT EXAMPLE 3

The same presenting history and indication as found in Treatment Example 2 is offered by a male 25 years of age. Upon oral administration of a single layer tablet containing 16 mg of metoclopramide and 1000 mg naproxen sodium the same result is obtained.

The metoclopramide and NSAID combined compositions of this invention can be made up of various agents including those listed herein. As an example, in the case of naproxen sodium and metoclopramide, several unit dosage form strengths are available including, but not limited to, 8 mg metoclopramide/500 mg naproxen sodium, 16 mg metoclopramide/500 mg naproxen sodium, 8 mg metoclopramide/250 mg naproxen sodium, 16 mg metoclopramide/250 mg naproxen sodium. Each dosage form has the dissolution characteristics described previously.

TREATMENT EXAMPLE 4

An adult female migraineur is complaining of a migraine attack consisting of typical migraine headache, nausea and sensitivity to light and sound. She is dosed with a tablet of Tablet Preparation, Example 4 containing metoclopramide 8 mg and naproxen sodium 500 mg. The naproxen moves from the stomach into the duodenum within 5 minutes of dosing. Her symptoms start to diminish within one hour and by three hours she is completely symptom free and has no relapse over the next 48 hours. She experiences fewer adverse events than when she ingested 875 mg of naproxen sodium alone, especially gastrointestinal complaints.

The metoclopramide and NSAID combined compositions of this invention possess valuable pharmacological properties. They provide non-vasoactive initial relief of migraine headache with fewer side effects and/or greater efficacy, depending on the doses of each agent employed. While inter-patient responsiveness to any drug therapy must be considered, this enhanced migraine treatment effect of the formulations of this invention can be demonstrated, for example, using the methods employed in the clinical studies reviewed by Plosker and McTavish, (*Drugs* 1994;47:622–651), Wilkinson et al. (*Cephalalgia* 1995;15:337–357), and Visser et al. (*Cephalalgia* 1996;1 6:264–269) the teachings of which are incorporated herein by reference.

The pharmacologically active compositions of this invention can be processed in accordance with conventional methods of Galenic pharmacy to produce medicinal agents for administration to patients, e.g., mammals including humans.

The compositions of this invention individually or in combination are employed in admixture with conventional excipients, i.e., pharmaceutically acceptable organic or inorganic carrier substances suitable for parenteral, enteral (e.g., oral or inhalation) which do not deleteriously react with the active compositions. Suitable pharmaceutically acceptable carriers include but are not limited to water, salt solutions, alcohols, gum Arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

In some embodiments of the present invention, dosage forms include instructions for the use of such compositions.

For non-parenteral applications, particularly suitable are tablets, dragees, liquids, drops, suppositories, or capsules. A syrup, elixir, or the like can be used wherein a sweetened vehicle is employed. Sublingual and buccal forms are also noted.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage form comprising about 1–30 mg of metoclopramide and about 200–1000 mg of naproxen sodium or equivalent doses of other NSAIDs in a pharmaceutically acceptable carrier per unit dosage.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

We claim:

1. An acid-base storage stable, uniform-coated, non-vasoactive, supra-vasoactive syndrome ("SVS") minimized, pharmaceutical unit dosage form for treatment of migraine in a human comprising:

(i) means for providing rapid availability metoclopramide to said humane upon administration in at least an effective local gastrointestinal amount for said treatment and (ii) means for providing at least one long acting NSAID to said human upon administration in a therapeutically effective amount for said treatment wherein said dosage form is a coordinated dosage form, and wherein the dosage form is absent 5HT agonist vasoactive agents.

2. An acid-base storage stable, uniform-coated, non-vasoactive, supra-vasoactive syndrome ("SVS") minimized, pharmaceutical unit dosage form for treatment of migraine in a human comprising:

(i) a first layer containing an NSAID in granular form uniformly distributed throughout a matrix of pharmaceutically acceptable fillers, excipients, binding agents, disintegrants, and lubricants, surrounded by (ii) a second layer having an interior and exterior portion, and having metoclopramide in crystalline form uniformly distributed throughout the exterior portion of said second layer wherein said interior portion comprises an interface between the exterior portion of said second layer the first layer, and wherein, (iii) said interior portion comprises from about 1% to about 15% of total tablet coating of said second layer.

3. The dosage form of claim 2 wherein said exterior portion of said second layer comprises talc in an amount at least about 20% by weight of the dry ingredients of said exterior portion.

4. A method of manufacturing a unit dosage form for treatment of migraine in a human comprising (i) forming over an NSAID core a coating layer having an interior and exterior portion by the steps of;

(ii) applying as the interior portion of said layer a coating of a weight equal to from about 1% to about 8% of the core weight, wherein said coating is a pharmaceutically acceptable coating material and said coating material is absent metoclopramide; and thereafter (iii) drying said interior portion; and thereafter, (iv) applying over said dried interior portion an exterior portion comprising a coating of a weight equal to from about 6% to about 15% of the core weight, wherein said coating comprises metoclopramide uniformly distributed throughout said exterior portion.

5. The method of claim 4 wherein the NSAID is naproxen sodium.

6. The method of claim 4 wherein the coating of step (iv) is applied by spray coating said exterior portion of a coating layer by rotating in a tablet coating pan the NSAID cores with interior coating layer applied, said rotating being at a speed of from about 10 to about 25 rpm, wherein said rotation is accompanied by spraying said coating material from one to a plurality of spray guns mounted about 10 to 12 inches apart and 4 to 8 inches above the rotating pan tablets until the cores increase in weight from about 4% to about 15%.

7. The method of 6 wherein said rotating is agitating rotating.

8. The method of claim 4 wherein the coating of step (iv) is applied by spray coating said exterior portion of a coating layer by rotating in a tablet coating pan the NSAID cores with interior coating layer applied, said rotating being at a speed of from about 10 to about 25 rpm, wherein said rotation is accompanied by spraying said coating material from one to a plurality of spray guns mounted about 10 to 12 inches apart and 4 to 8 inches above the rotating pan tablets until at least about 5 mg of metoclopramide are applied to each tablet.

9. The method of 8 wherein said rotating is agitating rotating.

* * * * *